United States Patent
Geng et al.

(10) Patent No.: US 10,023,906 B2
(45) Date of Patent: Jul. 17, 2018

(54) METHOD FOR CONSTRUCTING NUCLEIC ACID SINGLE-STRANDED CYCLIC LIBRARY AND REAGENTS THEREOF

(71) Applicant: BGI SHENZHEN CO., LIMITED, Shenzhen (CN)

(72) Inventors: Chunyu Geng, Shenzhen (CN); Rongrong Guo, Shenzhen (CN); Ruoying Chen, Shenzhen (CN); Lingyu He, Shenzhen (CN); Wenwei Zhang, Shenzhen (CN); Hui Jiang, Shenzhen (CN)

(73) Assignee: MGI Tech Co., Ltd., Shenzhen (CN)

( * ) Notice: Subject to any disclaimer, the term of this patent is extended or adjusted under 35 U.S.C. 154(b) by 0 days.

(21) Appl. No.: 15/510,904

(22) PCT Filed: Oct. 14, 2014

(86) PCT No.: PCT/CN2014/088543
§ 371 (c)(1),
(2) Date: Mar. 13, 2017

(87) PCT Pub. No.: WO2016/037394
PCT Pub. Date: Mar. 17, 2016

(65) Prior Publication Data
US 2018/0044667 A1 Feb. 15, 2018

Related U.S. Application Data

(63) Continuation-in-part of application No. PCT/CN2014/086418, filed on Sep. 12, 2014.

(51) Int. Cl.
*C12Q 1/68* (2018.01)
*C12N 9/22* (2006.01)
(Continued)

(52) U.S. Cl.
CPC ............ *C12Q 1/6853* (2013.01); *C12N 9/22* (2013.01); *C12N 9/93* (2013.01); *C12N 11/06* (2013.01);
(Continued)

(58) Field of Classification Search
CPC .... C12Q 1/6853; C12Q 1/686; C12Q 1/6806; C12Q 2565/537; C12N 15/66;
(Continued)

(56) References Cited

U.S. PATENT DOCUMENTS

2010/0120098 A1* 5/2010 Grunenwald .......... C12N 15/10
435/91.2

FOREIGN PATENT DOCUMENTS

CN 102264914 A 11/2011
CN 102296065 A 12/2011
(Continued)

OTHER PUBLICATIONS

International Search Report issued for PCT/CN2014/088543, dated Jun. 19, 2015.
(Continued)

*Primary Examiner* — Jeremy C Flinders
(74) *Attorney, Agent, or Firm* — Westman, Champlin & Koehler, P.A.; Z. Peter Sawicki; Amanda M. Prose (57) ABSTRACT

Provided in the present invention are a method for constructing a nucleic acid single-stranded cyclic library and reagent kit thereof. The method comprises the steps of using a transposase embedding complex to randomly break nucleic acids and connect a first linker; connecting a second linker at a gap; performing a first PCR reaction, wherein the 5' end of one of the primers has a first affinity tag, resulting in a product with two ends connected to different linker sequences; binding the product to a solid vector having a second affinity tag; degenerating and separating single
(Continued)

strands having no affinity tag; and cyclizing the single strands.

10 Claims, 3 Drawing Sheets

(51) Int. Cl.

| | | |
|---|---|---|
| *C12Q 1/6853* | (2018.01) | |
| *C12N 15/10* | (2006.01) | |
| *C40B 40/08* | (2006.01) | |
| *C12N 11/06* | (2006.01) | |
| *C12N 9/00* | (2006.01) | |
| *C12Q 1/686* | (2018.01) | |
| *C40B 50/06* | (2006.01) | |
| *C40B 50/14* | (2006.01) | |
| *C12Q 1/6806* | (2018.01) | |
| *C12N 15/66* | (2006.01) | |

(52) U.S. Cl.
CPC ..... *C12N 15/1065* (2013.01); *C12N 15/1082* (2013.01); *C12N 15/66* (2013.01); *C12Q 1/686* (2013.01); *C12Q 1/6806* (2013.01); *C40B 40/08* (2013.01); *C40B 50/06* (2013.01); *C40B 50/14* (2013.01); *C12Q 2565/537* (2013.01)

(58) Field of Classification Search
CPC .. C12N 15/1082; C12N 15/1065; C12N 9/93; C12N 11/06; C40B 40/08; C40B 50/14; C40B 50/06
See application file for complete search history.

(56) References Cited

FOREIGN PATENT DOCUMENTS

| | | | |
|---|---|---|---|
| CN | 102703426 A | 10/2012 | |
| CN | 102703432 A | 10/2012 | |
| CN | 103103624 A | 5/2013 | |
| CN | 103710323 A | 4/2014 | |
| EP | 2712931 A1 | 4/2014 | |
| WO | 01/40516 A2 | 6/2001 | |
| WO | 2004/070007 A2 | 8/2004 | |
| WO | 2007076420 A2 | 7/2007 | |
| WO | 2007140417 A2 | 12/2007 | |
| WO | 2008070375 A2 | 12/2007 | |
| WO | 2008070352 A2 | 6/2008 | |
| WO | 2009/061840 A1 | 5/2009 | |
| WO | 2009/120372 A2 | 10/2009 | |
| WO | 2010/048605 A1 | 4/2010 | |
| WO | 2011/112718 A1 | 9/2011 | |
| WO | 2012037876 A1 | 3/2012 | |
| WO | 2012037880 A1 | 3/2012 | |
| WO | 2012079486 A1 | 6/2012 | |

OTHER PUBLICATIONS

Written Opinion of the International Searching Authority issued for PCT/CN2014/088543, dated Jun. 19, 2015.
Ukai H., et al. "A new technique to prevent self-ligation of DNA" Journal of Biotechnology vol. 97, Dec. 31, 2002, pp. 233-242.
International Search Report issued for PCT/CN2014/086418, dated Jun. 15, 2015.
Written Opinion of the International Searching Authority issued for PCT/CN2014/088418, dated Jun. 15, 2015.
Hultman T et al., "Solid-phase cloning to create sublibraries suitable for DNA sequencing" Journal of Biotechnology, Elsevier, vol. 35, No. 2-3, pp. 229-238, 1994.
Bennett E A et al., "Library construction for ancient genomics: single strand or double strand?", Biotechniques Rapid Dispatches, Information Healthcare, US, vol. 56, No. 6, pp. 289-290, 2014.
Marie-Theres Gansauge et al., "Single-stranded DNA library preparation for the sequencing of ancient or damaged DNA", Nature Protocols, vol. 8, No. 4, pp. 737-748, 2013.
European Search Report issued for EP14901597.6, dated Jul. 4, 2017.

* cited by examiner

METHOD FOR CONSTRUCTING NUCLEIC ACID SINGLE-STRANDED CYCLIC LIBRARY AND REAGENTS THEREOF

CROSS-REFERENCE TO RELATED APPLICATION

This application is the U.S. national phase of PCT Application No. PCT/CN2014/088543 filed on Oct. 14, 2014, which claims a priority to and benefits of PCT Application No. PCT/CN2014/086418, filed with the State Intellectual Property Office of P. R. China on Sep. 12, 2014, the entire contents of which are incorporated herein by reference.

FIELD

The present disclosure relates to the field of molecular biology, particular to a method and a reagent kit for constructing a library containing single-stranded cyclic nucleic acids.

BACKGROUND

Exon sequencing, also known as target exome capturing, refers to a genome analysis method by which DNAs containing exon regions of a whole genome are captured by means of sequence region capture technology and subjected to high-throughput sequencing after enrichment. Exon sequencing is an efficient strategy for selecting coding sequences from the genome, which is less costly than genome resequencing, and has great advantages in studying mononucleotide polymorphism, insertion and deletion of known genes. An exon library commonly used is a library containing double-stranded DNAs for the Illumina platform or Proton platform which is roughly constructed according to protocols as follows: randomly fragmenting the genomic DNA into fragments of lengths ranging from 180 to 280 bp, ligating an adaptor at each terminal of the fragment subsequent to end-repairing and adding an adenine (A) tail, so as to construct a library. The library is subjected to first enrichment by first liquid hybridization with probes marked with biotin, then exons obtained after the first enrichment are captured by magnetic beads coated with streptomycin and then eluted from the magnetic beads to perform second enrichment by second liquid hybridization. The library obtained after twice enrichment is linear amplified by PCR reaction and can be sequenced after it is tested to be qualified.

Figure 1:
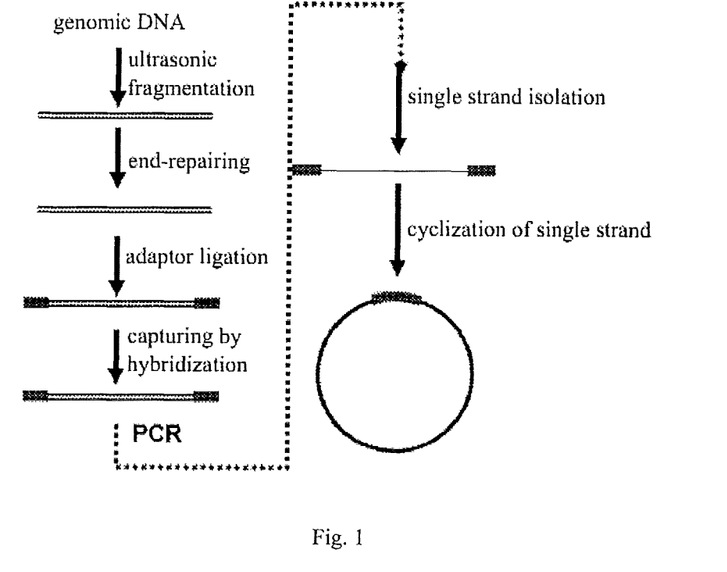
FIG. 1 is a flow chart showing a CG-based method for constructing a library with a single adaptor in the related art.

However, there is no reliable process for constructing the exon library used in Complete Genomics (CG) platform sequencing. A library construction method in the related art is such a method which is based on CG and by which a library is constructed with a single adaptor according to the protocol basically shown in FIG. 1: randomly fragmenting the genomic DNA into fragments of lengths within a certain range in a physical way, end-repairing and directionally ligating an adaptor A, liquid hybridizing with probes coated with biotin, capturing exons with magnetic beads coated with streptomycin, performing PCR amplification and isolating single-stranded nucleic acids; and finally cyclizing the single-stranded nucleic acid to obtain a library containing single-stranded cyclic nucleic acids. Such a method is complex and time-consuming, so there is still much room for improvement.

A transposase fragmentation kit, led by the Nextera kit from Epicentra company (purchased by Illumina), may complete DNA fragmentation and adaptor ligation at the same time by means of the transposase, thereby reducing the time for sample preparation. Such a fragmentation and adaptor ligation method may be used in the library construction.

In view of the simplicity of the various operations, transposase fragmentation is undoubtedly far superior to other methods in terms of throughput and operation simplicity. However, such fragmentation also has shortcomings. For example, transposition realized by the transposase depends on a specific 19 bp Me sequence. Therefore, though the transposase may ligate different adaptor sequences to a target sequence respectively at the 5'-terminal and the 3'-terminal by embedding two completely different adaptor sequences, the target sequence after fragmentation will symmetrically contain a Me sequence at each terminal thereof with a 9 nt gap formed between the target sequence (fragmented fragments) and Me sequence due to the special function of the transposase. However, the identical Me sequences at two terminals of the target sequence will have an adverse influence on downstream technology applications. For example, when combining this adaptor ligation with the next-generation sequencing technology, the fact that the Me sequences located at two ends of the same strand of the target sequence are complementary to each other, will easily result in internal annealing within one single-stranded molecule, thus adversely contributing to combination with an anchoring primer.

At present, there is an urgent need for a simple method for constructing a library containing single-stranded cyclic nucleic acids, especially suitable for exon sequencing.

SUMMARY

Embodiments of the present disclosure provide a method and a reagent kit for constructing a library containing single-stranded cyclic nucleic acids. Furthermore, such a method is simple and time saving, without adversely influenced by the identical transposase recognition sequences at two ends of the single-stranded nucleic acids.

According to embodiments of a first aspect of the present disclosure, a method for constructing a library containing single-stranded cyclic nucleic acids is provided, the method including:

randomly fragmenting a double-stranded nucleic acid sample with a transposase embedded complex, which includes transposase and a first adaptor containing a transposase recognition sequence, to obtain fragmented double-stranded nucleic acids ligated with the first adaptor at each terminal thereof, resulting in a gap between each 3'-end and the first adaptor;

ligating with ligase a second adaptor to the fragmented double-stranded nucleic acid at the gap after removing the transposase from the reaction system, the second adaptor having a sequence different from that of the first adaptor;

performing a first PCR reaction with a first pair of primers targeting the first adaptor and the second adaptor respectively, to obtain a first PCR product ligated with a first adaptor sequence and a second adaptor sequence respectively at two ends thereof, wherein one of the first pair of primers contains a first affinity marker at the 5'-end thereof;

contacting the first PCR product with a solid carrier having a second affinity marker, such that the first affinity marker is combined with the second affinity marker;

isolating single-stranded acids without the first affinity marker through denaturing the first PCR product combined nucleic with the solid carrier; and cyclizing the single-stranded nucleic acid with a single-stranded cyclization "bridge" sequence which is capable of combining with the two ends of the single-stranded nucleic acid.

In embodiments of the present disclosure, the method further includes: performing, prior to the first PCR reaction, a second PCR reaction with a second pair of primers targeting the first adaptor and the second adaptor respectively, to obtain a second PCR product ligated with the first adaptor sequence and the second adaptor sequence respectively at two ends thereof.

In embodiments of the present disclosure, one of the second pair of primers contains a sample-tag sequence at the 5'-end thereof.

In embodiments of the present disclosure, the method further includes a step subsequent to the second PCR reaction and prior to the first PCR reaction: capturing a single-stranded nucleic acid containing an exon sequence, used for the first PCR reaction, from the second PCR product with a probe for the exon sequence, wherein the probe for the exon sequence contains the first affinity marker and is capable of combining with the second affinity marker of the solid carrier.

In embodiments of the present disclosure, the method further includes: blocking a primer sequence located at each end of single strand of the second PCR product with a primer blocking sequence, prior to capturing the single-stranded nucleic acid containing the exon sequence of the second PCR product with the probe for the exon sequence.

In embodiments of the present disclosure, the first affinity marker is a biotin marker, and the second affinity marker is a streptavidin marker.

In embodiments of the present disclosure, the transposase is removed from the reaction system by magnetic beads purification, column purification or chemical reagent treatment.

In embodiments of the present disclosure, the solid carrier is magnetic beads.

In embodiments of the present disclosure, the method further includes:

randomly fragmenting a double-stranded nucleic acid sample with a transposase embedded complex, which includes transposase and a first adaptor containing a transposase recognition sequence, to obtain fragmented double-stranded nucleic acids ligated with the first adaptor at each terminal thereof, resulting in a gap between each 3'-end and the first adaptor;

ligating with ligase a second adaptor to the fragmented double-stranded nucleic acid at the gap after removing the transposase from the reaction system, the second adaptor having a sequence different from that of the first adaptor;

performing a second PCR reaction with a second pair of primers targeting the first adaptor and the second adaptor respectively, to obtain a second PCR product ligated with a first adaptor sequence and a second adaptor sequence respectively at two ends thereof, wherein one of the second pair of primers contains a sample-tag sequence at the 5'-end thereof;

blocking a primer sequence located at each end of single strand of the second PCR product with a primer blocking sequence;

capturing a single-stranded nucleic acid containing an exon sequence from the second PCR product with a probe for the exon sequence containing a biotin marker and capable of combining with a streptavidin marker of the solid carrier;

performing a first PCR reaction with a first pair of primers targeting two ends of the single-stranded nucleic acid containing the exon sequence respectively, to obtain a first PCR product ligated with different adaptor sequences respectively at two ends thereof, wherein one of the first pair of primers contains the biotin marker at the 5'-end thereof;

contacting the first PCR product with the solid carrier having the streptavidin marker, such that the biotin marker is combined with the streptavidin marker;

isolating single-stranded nucleic acids without the biotin marker through denaturing the first PCR product combined with the solid carrier; and cyclizing the single-stranded nucleic acid without the biotin marker with the single-stranded cyclization "bridge" sequence which is capable of combining with the two ends of the single-stranded nucleic acid without the biotin marker.

According to embodiments of a second aspect of the present disclosure, a reagent kit for constructing a library containing single-stranded cyclic nucleic acids is provided. The reagent kit includes:

a transposase embedded complex, formed with transposase and a first adaptor containing a transposase recognition sequence, and suitable for randomly fragmenting a double-stranded nucleic acid sample, to obtain fragmented double-stranded nucleic acids ligated with the first adaptor at each terminal thereof, resulting in a gap between each 3'-end and the first adaptor;

a component, comprising a second adaptor and ligase, and suitable for ligating the second adaptor to the fragmented double-stranded nucleic acid with ligases at the gap;

a first pair of primers, used in a first PCR reaction, and targeting the first adaptor and the second adaptor respectively, wherein one of the first pair of primers contains a first affinity marker at the 5'-end thereof;

a solid carrier, having a second affinity marker, suitable for combining with the first affinity marker;

a denaturation solution, suitable for denaturing a PCR product combined with the solid carrier so as to isolate single-stranded nucleic acids without the first affinity marker;

a single-stranded cyclization "bridge" sequence, capable of combining with two ends of the single-stranded nucleic acid, and suitable for cyclizing the single-stranded nucleic acid.

In embodiments of the present disclosure, the reagent kit further includes: a second pair of primers, used in a second PCR reaction, and targeting the first adaptor and the second adaptor respectively, preferably one of the second pair of primers contains a sample-tag sequence at the 5'-end thereof.

In embodiments of the present disclosure, the reagent combination further includes: a probe for an exon sequence, having the first affinity marker and capable of combining with the second affinity marker of the solid carrier, suitable for capturing single-stranded nucleic acids containing the exon sequence of a second PCR product; and preferably, the reagent combination further includes a primer blocking sequence, for blocking a primer sequence located at each end of the second PCR product.

In embodiments of the present disclosure, the first affinity marker is a biotin marker, and the second affinity marker is a streptavidin marker.

In embodiments of the present disclosure, the solid carrier is magnetic beads.

According to the technical solution provided in embodiments of the present disclosure, the current method includes fragmenting a double-stranded nucleic acid sample with a transposase and further ligating a second adaptor to the fragmented double-stranded nucleic acids, thereby obtaining double-stranded nucleic acids ligated with two different adaptor sequences respectively at the two ends. On this basis, the method further includes isolating and then cyclizing single-stranded nucleic acids, thereby obtaining the library containing single-stranded cyclic nucleic acids. Compared with the existing method, the method according to the present disclosure is simple and time saving, without adverse influence by identical transposase recognition sequences at two ends of the single-stranded nucleic acids.

DETAILED DESCRIPTION

The present disclosure will be described in further detail with reference to specific embodiments. The techniques used in embodiments below are conventional techniques known to those skilled in the art, unless specified otherwise. The instruments, equipment and reagents used herein are available to those skilled in the art through common ways, such as commercial purchase and so on.

Terms used herein are explained as follows: in specific embodiments, the first adaptor is referred to as adaptor No. 1, the second adaptor is referred to as adaptor No. 2.

In present disclosure, concepts such as "first" and "second" are used in any case only for purposes of distinguishing one from other subjects, and are not intended to indicate or imply relative sequence or technique.

The method for constructing the library containing single-stranded cyclic nucleic acids according to an embodiment of the present disclosure includes: randomly fragmenting a double-stranded nucleic acid sample with a transposase embedded complex, which comprises transposase and a first adaptor containing a transposase recognition sequence, to obtain fragmented double-stranded nucleic acids ligated with the first adaptor at each terminal thereof, resulting in a gap between each 3'-end and the first adaptor; ligating with ligase a second adaptor to the fragmented double-stranded nucleic acid at the gap after removing the transposase from the reaction system, the second adaptor having a sequence different from that of the first adaptor; performing a first PCR reaction with a first pair of primers targeting the first adaptor and the second adaptor respectively, to obtain a first PCR product ligated with a first adaptor sequence and a second adaptor sequence respectively at two ends thereof, wherein one of the first pair of primers contains a first affinity marker at the 5'-end thereof; contacting the first PCR product with a solid carrier having a second affinity marker, such that the first affinity marker is combined with the second affinity marker; isolating single-stranded nucleic acids without the first affinity marker through denaturing the first PCR product combined with the solid carrier; and cyclizing the single-stranded nucleic acid with a single-stranded cyclization "bridge" sequence which is capable of combining with two ends of the single-stranded nucleic acid.

The library containing single-stranded cyclic nucleic acids can be achieved regardless of exons or introns by the method described above. It is well known that a library containing single-stranded cyclic nucleic acids for a bacterial genome excluding introns can be constructed by the method described above, which can be further used in downstream operations, such as sequencing.

The method provided in embodiments of the present disclosure can fragment the nucleic acids and ligate the adaptor at the same time with the transposase embedded complex, which omits end-repairing, adaptor ligation and the intermediate purification step in a traditional process, thereby simplifying process and saving time.

In the present disclosure, the first adaptor contains the transposase recognition sequence, typically the well-known 19 bp Me sequence, and is present in double-stranded form, one strand of which may include a dideoxy modification (i.e dideoxynucleotide) at the 3'-end thereof to avoid self-ligation or inter-ligation. "Self-ligation" refers to such a ligation occurring between two adaptors of the same type, such as a ligation between two first adaptors or ligation between two second adaptors. "Inter-ligation" refers to such a ligation occurring between two adaptors of different types, such as a ligation between the first and second adaptors. The double-stranded nucleic acid sample is fragmented by the transposase embedded complex, after which a first strand of the first adaptor is ligated to a strand of the fragmented double-stranded nucleic acid, while between the other strand of the first adaptor and the other strand of the fragmented double-stranded nucleic acid, a gap of 9 nt is formed, which needs to be filled by nick translation in a conventional manner, whereas it just provides a ligation site for the second adaptor in the method of the present disclosure.

In the present disclosure, the sequence of the second adaptor may be any one different from that of the first adaptor, as the second adaptor used in the present disclosure is mainly to avoid the identical transposase recognition sequence located at two ends of the double-stranded nucleic acid. After the second adaptor is ligated at the gap, the first PCR product, ligated with the first adaptor sequence and the second adaptor sequence respectively at two ends thereof, may be obtained by performing the first PCR reaction with primers respectively targeting the first and second adaptors.

In the present disclosure, one of a first pair of primers used in the first PCR contains a first affinity marker at the 5'-end thereof, and the first affinity marker may be a component commonly used in biological binding reactions, such as an antigen or antibody, a strand of short double-stranded DNA fragment, biotin or streptavidin, and so on. In the case where an antigen is selected as the first affinity marker, an antibody which is capable of binding to the antigen is selected as the second affinity marker, and vice versa. In the case where one strand of short double-stranded DNA fragment is selected as the first affinity marker, the other complementary strand of the same short double-stranded DNA fragment is selected as the second affinity marker, and vice versa. In the case where biotin is selected as the first affinity marker, streptavidin which is capable of binding to the biotin is selected as the second affinity marker, and vice versa. In an embodiment of the present disclosure, the first affinity marker is biotin, and the second affinity marker is streptavidin, both of which have a strong binding capacity.

In the present disclosure, the single-stranded cyclization "bridge" sequence is such a sequence that is complementary with two ends of the single-stranded nucleic acid and thus bridges the two ends of the single-stranded nucleic acid, so as to achieve the cyclization of the single-stranded nucleic acid.

In a further embodiment of the present disclosure, the method further includes: performing, prior to the first PCR reaction, a second PCR reaction with a second pair of primers targeting the first adaptor and the second adaptor respectively. One purpose of the second PCR reaction is to massively amplify the fragmented double-stranded nucleic acids ligated with the first adaptor sequence and the second adaptor sequence respectively at two ends thereof. The second pair of primers may be identical in sequence to the first pair of primers except that there is no first affinity marker in the second pair of primers; the second pair of primers may be non-identical to the first pair of primers, for example, the second pair of primers may have extra bases at the 5'-end thereof as compared to the first pair of primers. A typical but unlimited example is that one of the second pair of primers contains a sample-tag sequence at the 5'-end thereof. The sample-tag sequence may be a random sequence for marking different samples, such that sequences from different samples can be distinguished after fragmenting, library construction and subsequent mixing for sequencing steps performed with several samples at the same time. This is because fragmented nucleic acids for each sample contain a specific sample-tag sequence.

Accordingly, sequencing efficiency is greatly improved in high-throughput sequencing. Therefore, in the case where one of the second pair of primers contains the sample-tag sequence, another purpose of the second PCR reaction is to ligate the sample-tag sequence to the fragmented double-stranded nucleic acid fragment.

In a further embodiment of the present disclosure, the method further includes: a step subsequent to the second PCR reaction and prior to the first PCR reaction: capturing a single-stranded nucleic acid containing an exon sequence from the second PCR product with a probe for the exon sequence. The exon capturing technology introduced in this embodiment is a well-known technology for obtaining the exon sequence. As some consensus sequences existing in exon and/or between exon and intron are conservative sequence, it is possible to design a probe for the exon sequence capable of binding with this consensus sequence, so as to isolate the single-stranded nucleic acid containing the exon sequence from various fragmented nucleic acids obtained after fragmenting numerous genomic DNA samples, for use in exon sequencing. In a specific embodiment of the present disclosure, the probe for the exon sequence needs to contain an affinity marker, e.g. biotin, such that the fragment containing the exon sequence may be isolated by the probe through the combination of the affinity marker and a solid carrier having the streptavidin marker.

In a further embodiment of the present disclosure, the method further includes: blocking a primer sequence located at each end of single strand of the second PCR product with a primer blocking sequence, prior to capturing the single-stranded nucleic acid containing the exon sequence of the second PCR product with the probe for the exon sequence. The primer blocking sequence is capable of specifically binding the primer sequence located at each end of single strand of the second PCR product, such that probe for the exon sequence cannot bind with such primer sequence, thereby avoiding a false positive result.

In the present disclosure, the solid carrier for capturing the fragment containing the exon sequences from the second PCR product and the solid carrier for combining the first PCR product may be a chip or magnetic beads. Specifically, the chip or magnetic bead carrier is coated with the second affinity marker which is capable of combining with the first affinity marker. In an embodiment of the present disclosure, the magnetic beads coated with the streptavidin marker are used.

In the present disclosure, after the double-stranded nucleic acid sample is fragmented, the transposase needs to be removed from the reaction system generally by magnetic beads purification, column purification or chemical reagent treatment to eliminate effect on the subsequent enzymatic reactions. Magnetic beads purification with such as Ampure XP beads and the column purification with such as purification columns from QIAGEN PCR are traditional purification methods, which are well-known in the related art. Undoubtedly, any similar product for magnetic beads purification and column purification may be used in the present disclosure. The purification can completely remove transposase from the reaction system, but will increase the corresponding operations and cost. The transposase can be dissociated from the target sequences through denaturation or digestion by chemical reagent treatment due to its protein nature, and will have lost its biological activity after this treatment, thus will not have a negative impact on the subsequent reaction, even if it still remains in the system.

In the present disclosure, during the chemical reagent treatment, protease solution, sodium dodecyl sulfate (SDS) solution, NT buffer (NT buffer included in a Truprep kit in S5 series) and the like may be firstly chosen to break the adsorption between the transposase and the nucleic acid target sequence, then a solution containing Triton-X100 is used to lower an adverse influence of the above reagent on the following enzymatic reaction. With this method, the traditional magnetic beads purification and column purification with complex processes and high cost will be replaced, and the downstream PCR amplification will be smoothly carried out.

In the present disclosure, the PCR product captured by the solid carrier may be denatured by heat or alkali, preferably alkali, such as sodium hydroxide or potassium hydroxide. In an embodiment of the present disclosure, sodium hydroxide is used.

Figure 2:
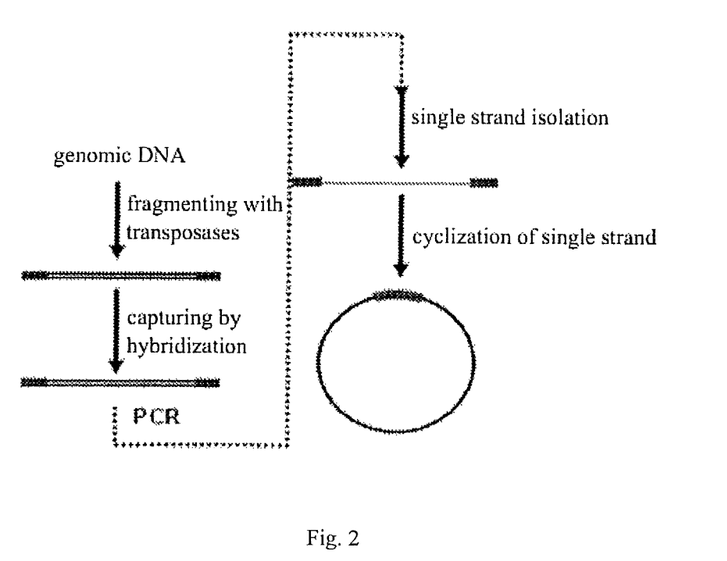
FIG. 2 is a simplified flow chart showing a method for constructing an exon library with transposase and a single adaptor, according to an embodiment of the present disclosure.

With reference to FIG. 2, a simplified flow chart showing the method for constructing an exon library with transposase and a single adaptor according to an embodiment of the present disclosure includes: fragmenting a genomic DNA sample with transposase to obtain fragmented fragments; amplifying the fragmented fragments by a second PCR reaction and capturing fragments containing exon sequences through the exon capturing technology; performing a first PCR reaction and isolating single-stranded nucleic acids; and cyclizing the single-stranded nucleic acids to obtain the library containing single-stranded cyclic nucleic acids.

Figure 3:
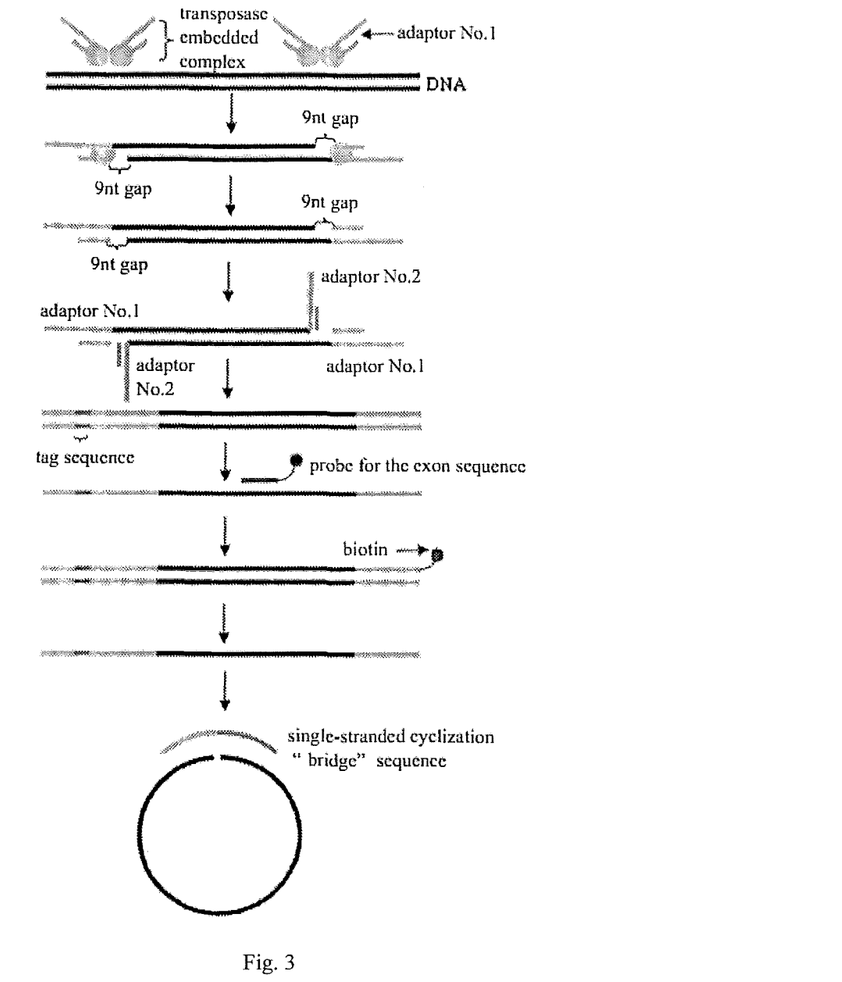
FIG. 3 is a detailed flow chart showing a method for constructing an exon library with a transposase and a single adaptor, according to an embodiment of the present disclosure.

With reference to FIG. 3, a detailed flow chart showing a method for constructing an exon library with transposase and a single adaptor according to an embodiment of the present disclosure includes: fragmenting a genomic DNA sample with a transposase embedded complex to obtain fragmented double-stranded DNAs ligated with a first adaptor at each terminal thereof, resulting in a 9 nt gap between each 3'-end and the first adaptor; removing the transposase; ligating a second adaptor; performing a second PCR amplification with a second pair of primers, one of which contains a tag sequence, to obtain a second amplification product containing the tag sequence; capturing a fragment containing an exon sequence with a probe for the exon sequence (containing a biotin marker); performing a first PCR amplification with a first pair of primers, one of which contains a biotin marker, to obtain a first amplification product containing the biotin marker at one strand thereof; isolating the product containing the biotin marker with magnetic beads coated with streptomycin; obtaining a single-stranded nucleic acid without the biotin marker through denaturation; cyclizing the single-stranded nucleic acid without the biotin marker with a single-stranded cyclization "bridge" sequence to obtain the library containing single-stranded cyclic nucleic acids.

In the following, the present disclosure will be described in detail with reference to embodiments.

Reagents used in embodiments of the present disclosure are explained as follows: ligases were purchased from INVITROGEN; transposases (including PCR enzyme) were contained in TruePrep Advanced DNA Sample Prep Kit purchased from Vazyme Biotech; Exonuclease I and Exonuclease III were purchased from NEB.

In the present embodiment, a transposase kit was used for technology development, which included genomic DNA in two amounts, 5 ng and 50 ng. The latter was chosen in the present embodiment.

1. A pair of primer sequences (sequence A and sequence B of Adaptor No. 1) containing the 19 bp Me sequence was designed and purchased for the preparation of Adaptor No. 1 for embedding, in which dideoxy thymine (T) base contained in sequence B can efficiently avoid the self-ligation of adaptors:

Sequence A of adaptor No. 1: GCTTCGACTGGA-GACAGATGTGTATAAGAGACAG (SEQ ID NO: 1);

Sequence B of adaptor No. 1: CTGTCTCTTATACA-CATC ddT (SEQ ID NO: 2).

2. The sequence A and sequence B of the adaptor No. 1 were diluted to 100 μM, centrifuged after sufficiently mixing, and then annealed in the PCR apparatus according to the following procedures (Table 1) to obtain adaptor No. 1, which was stored at −20° C. for the preparation of the transposase embedded complex.

TABLE 1

| Temperature | Time |
| --- | --- |
| 75° C. | 15 min |
| 60° C. | 10 min |
| 50° C. | 10 min |
| 40° C. | 10 min |
| 25° C. | 30 min |

Hot lid 105° C.

After the reaction, two groups of annealed adaptors were mixed at a volume ration of 1:1, for the preparation of the transposase embedded complex.

3. The components shown in the following system (Table 2) was mixed by gently blowing up and down for 20 times and then incubated at 30° C. for 1 hour to embed the adaptor No. 1 into the transposase, thus obtaining the transposase embedded complex, which was stored at −20° C.

TABLE 2

| Component | Amount |
| --- | --- |
| Transposase | 85 μL |
| Adaptor No. 1 | 30 μL |
| Coupling buffer | 85 μL |
| Total | 200 μL |

4. 50 ng genomic DNA with high quality was mixed with the transposase embedded complex together with other components shown in Table 3 by gently blowing up and down for 20 times, followed by incubation at 55° C. for 10 min and subsequently cooling down to 4° C., such that the genomic DNA was fragmented.

TABLE 3

| Component | Amount |
| --- | --- |
| Water | 5 μL |
| 5x Fragmenting buffer | 2 μL |
| gDNA (50 ng/μL) | 1 μL |
| transposase embedded complex | 2 μL |
| Total | 10 μL |

5. Purification was performed according to the following two methods:

Method 1: Fragmented genomes obtained above were firstly mixed with SDS in a final concentration of 0.04% to 0.1% to be uniform, then purified with Ampure XP beads in 1.3 folds;

Method 2: Fragmented genomes obtained above were firstly mixed with PBI (Qiagen PCR purification kit) in one fold in volume to be uniform, then purified with Ampure XP beads in 1.3 folds;

Method 3 (without purification): Fragmented genomes obtained above were added with SDS in a final concentration of 0.04% to 0.1%, and added with 0.1% Triton-X100 in the next enzymatic reaction.

6. The purified product obtained in previous step was incubated with components shown in Table 4 at 25° C. for 60 min for ligating the adaptor No. 2.

TABLE 4

| Component | Amount |
| --- | --- |
| Water | 8 μL |
| 3× Ligation buffer | 20 μL |
| Adaptor No.2 (5 μM) | 10 μL |
| Ligase | 2 μL |
| DNA | 20 μL |
| Total | 30 μL |

Note:
sequences of adaptor No. 2 is shown as follows:
Sequence A of adaptor No. 2: AGTCGGAGGCCAAGCGGTCGTC (SEQ ID NO: 3);
Sequence B of adaptor No. 2: TTGGCCTCCGAC ddT (SEQ ID NO: 4, dd represents dideoxy modification at the 3'-end).

7. The following process was performed:

Method 1 (purification): purification was performed with Ampure XP beads in 1.3 folds;

Method 2 (without purification): 1% Triton-X100 was complemented for the next PCR reaction.

8. 0.1%-2% Triton-X100, preferably 0.1% Triton-X100 in this embodiment, was mixed with the following components (Table 5), the obtained mixture was subjected to a first PCR amplification under conditions shown in Table 6. Primers containing different tags were designed for region (tag) capture directly subsequent to purification to mixing PCR products.

TABLE 5

| Component | Amount |
|---|---|
| DNA | 30 μL |
| 5× PCR buffer | 10 μL |
| 10 mM dNTPs | 1 μL |
| Tagged primers 1-8 | 2 μL |
| Primer 2 | 2 μL |
| PCR enzyme | 1 μL |
| Pure Water | 4 μL |
| Total | 50 μL |

Note:
Tagged primers 1-8 are shown as follows, where underline sequences represent tag sequences (random sequences):
Tagged primer 1 (SEQ ID NO: 5):
AGACAAGCTCGAGCTCACTGGTAAGAGCTTCGACTGGAGAC
Tagged primer 2 (SEQ ID NO: 6):
AGACAAGCTCGAGCTCAAGCTCCTGAGCTTCGACTGGAGAC
Tagged primer 3 (SEQ ID NO: 7):
AGACAAGCTCGAGCTCCTGGGGCTATGCTTCGACTGGAGAC
Tagged primer 4 (SEQ ID NO: 8):
AGACAAGCTCGAGCTCCCCAGTCAGGGCTTCGACTGGAGAC
Tagged primer 5 (SEQ ID NO: 9):
AGACAAGCTCGAGCTCGGATTTGGTTGCTTCGACTGGAGAC
Tagged primer 6 (SEQ ID NO: 10):
AGACAAGCTCGAGCTCTACTAATGGCGCTTCGACTGGAGAC
Tagged primer 7 (SEQ ID NO: 11):
AGACAAGCTCGAGCTCTTTTCATTTTGCTTCGACTGGAGAC
Tagged primer 8 (SEQ ID NO: 12):
AGACAAGCTCGAGCTCCTGAGCTCCTGCTTCGACTGGAGAC
Primer 2 (SEQ ID NO: 13):
TCCTAAGACCGCTTGGCCTCCGACT

TABLE 6

| Temperature | Time | cycle |
|---|---|---|
| 95° C. | 30 min | 1 cycle |
| 95° C. | 10 sec | 12 cycles |
| 56° C. | 30 sec | |
| 72° C. | 3 min | |
| 68° C. | 10 min | 1 cycle |
| 4° C. | ∞ | — |

After the second PCR, 8 samples containing different tags were mixed and then purified with Ampure XP beads in 1.3 folds.

9. 750 ng sample obtained in previous step was concentrated into dry powder.

Reaction mixture 1 was prepared in accordance with the following steps:

(1) Formulating the following reaction solution (Table 7):

TABLE 7

| Component | Amount |
|---|---|
| Blocking sequence#1 (SureSelect Block#1, Agilent Company) | 2.5 μL |
| Blocking sequence#2 (SureSelect Block#2, Agilent Company) | 2.5 μL |
| Primer Blocking sequence#1 | 0.3 μL |
| Primer blocking sequence#2 | 0.3 μL |
| Pure Water | 3.4 μL |
| Total | 9 μL |

Note:
Primer blocking sequence#1 (SEQ ID NO: 14):
5'-CTGTCTCTTATACACATCTGTCTCCAGTCGAAGCCCGATCTTACCAGTTC-GAGCTTGTCT-3';
Primer blocking sequence#2 (SEQ ID NO: 15):
5'-AAGTCGGAGGCCAACGGTCTTAGGA-3'.

Blocking sequence#1 and blocking sequence#2 were oligonucleotide sequences (Oligo) contained in a kit purchased from Agilent Company, which was used for blocking some tandem repeats in the human genome.

(2) The reaction solution obtained in (1) was mixed with the dry powder sample to obtain a uniform reaction mixture 1, which was incubated in PCR instrument at 95° C. for 5 min, and then held at 65° C.

(3) Reaction mixture 2 was formulated in accordance with Table 8, then incubated in the PCR instrument at 65° C. for at least 5 min

TABLE 8

| Component | Amount |
|---|---|
| Hybridization solution#1 (SureSelect Hyb # 1, Agilent Company) | 25 μL |
| Hybridization solution#2 (SureSelect Hyb # 2, Agilent Company) | 1 μL |
| Hybridization solution#3 (SureSelect Hyb # 3, Agilent Company) | 10 μL |
| Hybridization solution#4 (SureSelect Hyb # 4, Agilent Company) | 13 μL |
| Total | 49 μL |

(4) Reaction mixture 3 was formulated in accordance with Table 9, then incubated in the PCR instrument at 65° C. for at least 2 min

TABLE 9

| Component | Amount |
|---|---|
| Rnase blocking solution (SureSelect RNase Block, Agilent Company) | 1 μL |
| Biotin hybridization probe (SureSelect Oligo Capture Library, Agilent Company) | 5 μL |
| Pure Water | 1 μL |
| Total | 7 μL |

Note:
The biotin hybridization probe, also referred to as the probe for the exon sequence in other places of the present disclosure, was used to capture the single-stranded fragment containing exon sequence.

(5) Reaction mixtures 1-3 all were held at 65° C. 13 μL reaction mixture 2 was added into the reaction mixture 1 to obtain a uniform mixture, which was then transferred into the reaction mixture 3 for hybridization for 24 hours after sealed by film.

10. Sample obtained after hybridization for 24 hours was eluted with M280 magnetic beads (i.e. magnetic beads coated with streptomycin), then subjected to first PCR without isolating M280 magnetic beads by using the following components (Table 10) and according to reaction conditions shown in Table 11, to amplify the product up to an amount of 600 ng and introduce biotin at the end where adaptor No. 2 was located for the next single strand isolation step.

TABLE 10

| Component | Amount |
|---|---|
| DNA | 120 μL |
| 5× PCRbuffer | 40 μL |
| 10 mM dNTPs | 4 μL |
| universal primer 1 | 8 μL |
| Primer 2 containing biotin | 8 μL |

TABLE 10-continued

| Component | Amount |
|---|---|
| PCR enzyme | 4 μL |
| Pure Water | 16 μL |
| Total | 200 μL |

Note:
universal primer 1: 5'-AGACAAGCTCGAGCTC-3' (SEQ ID NO: 16);
Primer 2 containing biotin:
5'-bio-TCCTAAGACCGCTTGGCCTCCGACT-3' (SEQ ID NO: 17).

TABLE 11

| Temperature | Time | cycle |
|---|---|---|
| 95° C. | 30 min | 1 cycle |
| 95° C. | 10 sec | 12 cycles |
| 56° C. | 30 sec | |
| 72° C. | 3 min | |
| 68° C. | 10 min | 1 cycle |
| 4° C. | ∞ | — |

After PCR, the amplified product was purified with Ampure XP beads in 1.3 folds.

11. 600 ng purified product was incubated with M280 magnetic beads coated with streptomycin for 15 min, then washed twice on a magnetic separator, finally denatured with 78 μL 0.1M NaOH solution, after which NaOH solution was recycled and the residual NaOH solution was neutralized with 37.5 μL 0.3M MOPS (3-(N-morpholino)propanesulfonic acid, SIGMA) buffer.

12. Cyclization of the single-stranded nucleic acid

A reaction system was formulated in according to Table 12, and incubated at 37° C. for 1.5 h.

TABLE 12

| Component | Amount |
|---|---|
| "Bridge" sequence | 20 μL |
| Pure Water | 178.3 μL |
| 10× ligation buffer | 35 μL |
| 100 mM ATP | 3.5 μL |
| Ligase | 1.2 μL |
| Single-stranded DNA recycled in previous step | 112 μL |
| Total | 350 μL |

Note:
"Bridge" sequence: 5'-TCGAGCTTGTCTTCCTAAGACCGC-3' (SEQ ID NO: 18).

13. Digestion of uncyclized single-stranded nucleic acids

A mixture was formulated in according to Table 13, and then added into the reaction system obtained in previous step after transient centrifugation, followed by incubated at 37° C. for 30 min

TABLE 13

| Component | Amount |
|---|---|
| 10× ligation buffer | 3.7 μL |
| 20 U/μL Exonuclease I | 11.1 μL |
| 100 U/μL Exonuclease III | 5.2 μL |
| Total | 20 μL |

Figure 4:
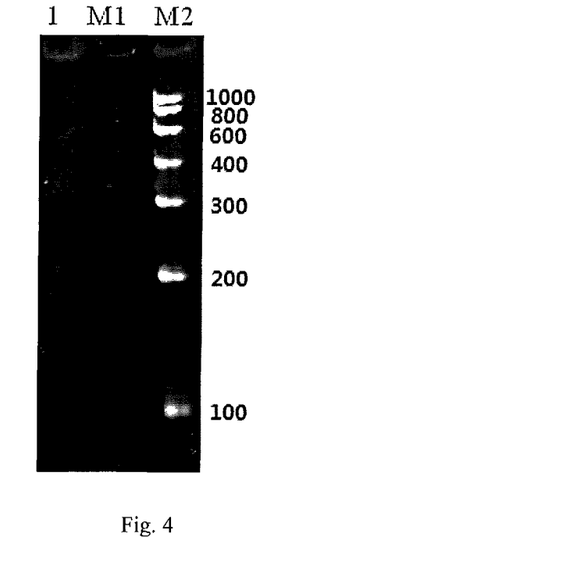
FIG. 4 is a diagram showing electrophoresis detection for a library containing single-stranded cyclic nucleic acids according to an embodiment of the present disclosure, where lane 1 represents a cyclic single-stranded product obtained in this embodiment; and M1 and M2 represent two markers of cyclic single-stranded DNAs.

14. Product (i.e. single-stranded cyclic nucleic acids) obtained after digestion of the uncyclized single-stranded nucleic acids was purified with Ampure XP beads in 1.8 folds. The purified product was sequenced when the solubility thereof was detected to be qualified. 0.65 pmol product was obtained in this embodiment, which is sufficient to be made into DNA nanospheres for whole genome sequencing. A small amount of purified product was taken for electrophoretic detection. The result is shown in FIG. 4, where lane 1 indicates that the single-stranded cyclic nucleic acids obtained in this embodiment show as a dispersive band with a size between 600 and 800 nt as expected, thus meeting the requirement for a library containing single-stranded cyclic nucleic acids.

TABLE 14

| Parameter | Value |
|---|---|
| Concentration | 1.62 ng/μL |
| Volume | 40 μL |
| Total amount | 64.8 ng |
| Mole number | 0.65 pmol |

15. The above library was sequenced on CG sequencer, and the sequencing results are show in Table 15.

TABLE 15

| Parameter | Value |
|---|---|
| Cover degree | 98.6% |
| SNP number | 42000 |
| Consistency of dbSNP data | 98.65% |
| Genotyping consistency | 99.97% |

Figure 5:
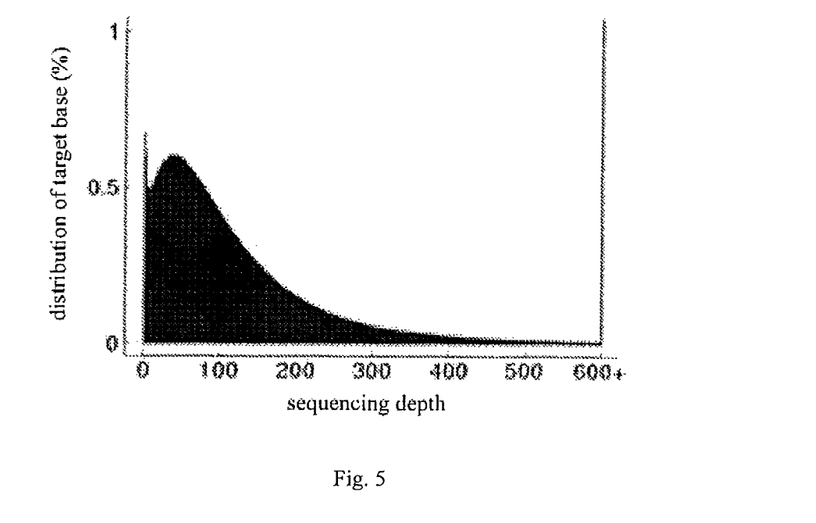
FIG. 5 is a diagram showing distribution of cumulative cover depth of a single base obtained by sequencing a library containing single-stranded cyclic nucleic acids according to an embodiment of the present disclosure.

Diagram showing the distribution of cumulative cover depth of single base is shown in FIG. 5. The above results indicate that the library containing single-stranded cyclic nucleic acids constructed as in above embodiment of the present disclosure can be successfully used for sequencing and achieve desirable results.

The above content is a further detailed description of the present disclosure in combination with the specific embodiments. However, the specific embodiments of the present disclosure shall not be limited to these instructions. It would be appreciated by those skilled in the art that some simple deductions or replacements can be made in the embodiments without departing from the spirit, principles and scope of the present disclosure.

What is claimed is:

1. A method for constructing a library containing single-stranded cyclic nucleic acids, comprising:

randomly fragmenting a double-stranded nucleic acid sample with a transposase embedded complex, which comprises transposases and a first adaptor containing a transposase recognition sequence, to obtain fragmented double-stranded nucleic acids ligated with the first adaptor at each terminal thereof, resulting in a gap between each 3'-end and the first adaptor;

ligating with ligase a second adaptor to the fragmented double-stranded nucleic acid at the gap after removing the transposase from the reaction system, the second adaptor having a sequence different from that of the first adaptor;

performing a first PCR reaction with a first pair of primers targeting the first adaptor and the second adaptor respectively, to obtain a first PCR product ligated with a first adaptor sequence and a second adaptor sequence respectively at two ends thereof, wherein one of the first pair of primers contains a first affinity marker at the 5'-end thereof;

contacting the first PCR product with a solid carrier having a second affinity marker, such that the first affinity marker is combined with the second affinity marker;

isolating single-stranded nucleic acids without the first affinity marker through denaturing the first PCR product combined with the solid carrier; and cyclizing the single-stranded nucleic acid with a single-stranded cyclization "bridge" sequence which is capable of combining with two ends of the single-stranded nucleic acid.

2. The method according to claim 1, further comprising: performing, prior to the first PCR reaction, a second PCR reaction with a second pair of primers targeting the first adaptor and the second adaptor respectively, to obtain a second PCR product ligated with the first adaptor sequence and the second adaptor sequence respectively at two ends thereof.

3. The method according to claim 2, wherein one of the second pair of primers contains a sample-tag sequence at the 5'-end thereof.

4. The method according to claim 2, further comprising a step subsequent to the second PCR reaction and prior to the first PCR reaction: capturing a single-stranded nucleic acid containing an exon sequence, used for the first PCR reaction, from the second PCR product with a probe for the exon sequence, wherein the probe for the exon sequence contains the first affinity marker and is capable of combining with the second affinity marker of the solid carrier.

5. The method according to claim 4, further comprising: blocking a primer sequence located at each end of single strand of the second PCR product with a primer blocking sequence, prior to capturing the single-stranded nucleic acid containing the exon sequence of the second PCR product with the probe for the exon sequence.

6. The method according to claim 1, wherein the first affinity marker is a biotin marker, and the second affinity marker is a streptavidin marker.

7. The method according to claim 1, wherein the transposase is removed from the reaction system by magnetic beads purification, column purification or chemical reagent treatment.

8. The method according to claim 1, wherein the solid carrier is magnetic beads.

9. The method according to claim 1, comprising:

randomly fragmenting a double-stranded nucleic acid sample with a transposase embedded complex, which comprises transposase and a first adaptor containing a transposase recognition sequence, to obtain fragmented double-stranded nucleic acids ligated with the first adaptor at each terminal thereof, resulting in a gap between each 3'-end and the first adaptor;

ligating with a ligase a second adaptor to the fragmented double-stranded nucleic acid at the gap after removing the transposase from the reaction system, the second adaptor having a sequence different from that of the first adaptor;

performing a second PCR reaction with a second pair of primers targeting the first adaptor and the second adaptor respectively, to obtain a second PCR product ligated with a first adaptor sequence and a second adaptor sequence respectively at two ends thereof, wherein one of the second pair of primers contains a sample-tag sequence at the 5'-end thereof;

blocking a primer sequence located at each end of single-strand of the second PCR product with a primer blocking sequence;

capturing a single-stranded nucleic acid containing an exon sequence from the second PCR product with a probe for the exon sequence containing a biotin marker and capable of combining with a streptavidin marker of the solid carrier;

performing a first PCR reaction with a first pair of primers targeting two ends of the single-stranded nucleic acid containing the exon sequence respectively, to obtain a first PCR product ligated with different adaptor sequences respectively at two ends thereof, wherein one of the first pair of primers contains the biotin marker at the 5'-end thereof;

contacting the first PCR product with the solid carrier having a streptavidin marker, such that the biotin marker is combined with the streptavidin marker;

isolating single-stranded nucleic acids without the biotin marker through denaturing the first PCR product combined with the solid carrier;

cyclizing the single-stranded nucleic acid without the biotin marker with a single-stranded cyclization "bridge" sequence which is capable of combining with the two ends of the single-stranded nucleic acid without the biotin marker.

10. The method according to claim 3, further comprising a step subsequent to the second PCR reaction and prior to the first PCR reaction: capturing a single-stranded nucleic acid containing an exon sequence, used for the first PCR reaction, from the second PCR product with a probe for the exon sequence, wherein the probe for the exon sequence contains the first affinity marker and is capable of combining with the second affinity marker of the solid carrier.

* * * * *

SEQUENCE LISTING

<160> NUMBER OF SEQ ID NOS: 18

<210> SEQ ID NO 1
<211> LENGTH: 34
<212> TYPE: DNA
<213> ORGANISM: Artificial sequence
<220> FEATURE:

<223> OTHER INFORMATION: Sequence A of adaptor No. 1

<400> SEQUENCE: 1
gcttcgactg gagacagatg tgtataagag acag                          34

<210> SEQ ID NO 2
<211> LENGTH: 19
<212> TYPE: DNA
<213> ORGANISM: Artificial sequence
<220> FEATURE:
<221> NAME/KEY: modified_base
<222> LOCATION: (19)..(19)
<223> OTHER INFORMATION: Dideoxy modification
<220> FEATURE:
<223> OTHER INFORMATION: Sequence B of adaptor No.1

<400> SEQUENCE: 2
ctgtctctta tacacatct                                           19

<210> SEQ ID NO 3
<211> LENGTH: 22
<212> TYPE: DNA
<213> ORGANISM: Artificial sequence
<220> FEATURE:
<223> OTHER INFORMATION: Sequence A of adaptor No.2

<400> SEQUENCE: 3
agtcggaggc caagcggtcg tc                                       22

<210> SEQ ID NO 4
<211> LENGTH: 13
<212> TYPE: DNA
<213> ORGANISM: Artificial sequence
<220> FEATURE:
<221> NAME/KEY: modified_base
<222> LOCATION: (13)..(13)
<223> OTHER INFORMATION: Dideoxy modification
<220> FEATURE:
<223> OTHER INFORMATION: Sequence B of adaptor No.2

<400> SEQUENCE: 4
ttggcctccg act                                                 13

<210> SEQ ID NO 5
<211> LENGTH: 41
<212> TYPE: DNA
<213> ORGANISM: Artificial sequence
<220> FEATURE:
<223> OTHER INFORMATION: Tagged primer 1

<400> SEQUENCE: 5
agacaagctc gagctcactg gtaagagctt cgactggaga c                  41

<210> SEQ ID NO 6
<211> LENGTH: 41
<212> TYPE: DNA
<213> ORGANISM: Artificial sequence
<220> FEATURE:
<223> OTHER INFORMATION: Tagged primer 2

<400> SEQUENCE: 6
agacaagctc gagctcaagc tcctgagctt cgactggaga c                  41

<210> SEQ ID NO 7
<211> LENGTH: 41
<212> TYPE: DNA
<213> ORGANISM: Artificial sequence -continued

```
<220> FEATURE:
<223> OTHER INFORMATION: Tagged primer 3

<400> SEQUENCE: 7
agacaagctc gagctcctgg ggctatgctt cgactggaga c        41

<210> SEQ ID NO 8
<211> LENGTH: 41
<212> TYPE: DNA
<213> ORGANISM: Artificial sequence
<220> FEATURE:
<223> OTHER INFORMATION: Tagged primer 4

<400> SEQUENCE: 8
agacaagctc gagctcccca gtcagggctt cgactggaga c        41

<210> SEQ ID NO 9
<211> LENGTH: 41
<212> TYPE: DNA
<213> ORGANISM: Artificial sequence
<220> FEATURE:
<223> OTHER INFORMATION: Tagged primer 5

<400> SEQUENCE: 9
agacaagctc gagctcggat ttggttgctt cgactggaga c        41

<210> SEQ ID NO 10
<211> LENGTH: 41
<212> TYPE: DNA
<213> ORGANISM: Artificial sequence
<220> FEATURE:
<223> OTHER INFORMATION: Tagged primer 6

<400> SEQUENCE: 10
agacaagctc gagctctact aatggcgctt cgactggaga c        41

<210> SEQ ID NO 11
<211> LENGTH: 41
<212> TYPE: DNA
<213> ORGANISM: Artificial sequence
<220> FEATURE:
<223> OTHER INFORMATION: Tagged primer 7

<400> SEQUENCE: 11
agacaagctc gagctctttt cattttgctt cgactggaga c        41

<210> SEQ ID NO 12
<211> LENGTH: 41
<212> TYPE: DNA
<213> ORGANISM: Artificial sequence
<220> FEATURE:
<223> OTHER INFORMATION: Tagged primer 8

<400> SEQUENCE: 12
agacaagctc gagctcctga gctcctgctt cgactggaga c        41

<210> SEQ ID NO 13
<211> LENGTH: 25
<212> TYPE: DNA
<213> ORGANISM: Artificial sequence
<220> FEATURE:
<223> OTHER INFORMATION: Primer 2

<400> SEQUENCE: 13
tcctaagacc gcttggcctc cgact                          25
```

<210> SEQ ID NO 14
<211> LENGTH: 60
<212> TYPE: DNA
<213> ORGANISM: Artificial sequence
<220> FEATURE:
<223> OTHER INFORMATION: Primer blocking sequence#1

<400> SEQUENCE: 14
ctgtctctta tacacatctg tctccagtcg aagcccgatc ttaccagttc gagcttgtct    60

<210> SEQ ID NO 15
<211> LENGTH: 26
<212> TYPE: DNA
<213> ORGANISM: Artificial sequence
<220> FEATURE:
<223> OTHER INFORMATION: Primer blocking sequence#2

<400> SEQUENCE: 15
aagtcggagg ccaagcggtc ttagga    26

<210> SEQ ID NO 16
<211> LENGTH: 16
<212> TYPE: DNA
<213> ORGANISM: Artificial sequence
<220> FEATURE:
<223> OTHER INFORMATION: universal primer 1

<400> SEQUENCE: 16
agacaagctc gagctc    16

<210> SEQ ID NO 17
<211> LENGTH: 25
<212> TYPE: DNA
<213> ORGANISM: Artificial sequence
<220> FEATURE:
<221> NAME/KEY: modified_base
<222> LOCATION: (1)..(1)
<223> OTHER INFORMATION: labeled with biotin
<220> FEATURE:
<223> OTHER INFORMATION: Primer 2 containing biotin

<400> SEQUENCE: 17
tcctaagacc gcttggcctc cgact    25

<210> SEQ ID NO 18
<211> LENGTH: 24
<212> TYPE: DNA
<213> ORGANISM: Artificial sequence
<220> FEATURE:
<223> OTHER INFORMATION: "Bridge sequence"

<400> SEQUENCE: 18
tcgagcttgt cttcctaaga ccgc    24